United States Patent
Neff et al.

(10) Patent No.: US 10,926,049 B2
(45) Date of Patent: Feb. 23, 2021

(54) PATIENT INTERFACE DEVICE WITH FRAME AND CLIPS

(71) Applicant: KONINKLiJKE PHILIPS N.V., Eindhoven (NL)

(72) Inventors: Adam Michael Neff, Oakmont, PA (US); Daniel James Miller, Cranberry Township, PA (US); Matthew Paul Eury, Latrobe, PA (US); Susan Marie Mals, Monroeville, PA (US); Timotheos James Leahy, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 556 days.

(21) Appl. No.: 14/431,312

(22) PCT Filed: Oct. 1, 2013

(86) PCT No.: PCT/IB2013/059028
§ 371 (c)(1),
(2) Date: Mar. 26, 2015

(87) PCT Pub. No.: WO2014/053987
PCT Pub. Date: Apr. 10, 2014

(65) Prior Publication Data
US 2015/0246200 A1 Sep. 3, 2015

Related U.S. Application Data

(60) Provisional application No. 61/708,770, filed on Oct. 2, 2012.

(51) Int. Cl.
*A61M 16/06* (2006.01)
*A61M 16/08* (2006.01)

(52) U.S. Cl.
CPC .... *A61M 16/0622* (2014.02); *A61M 16/0611* (2014.02); *A61M 16/0683* (2013.01); *A61M 16/0816* (2013.01); *A61M 2205/42* (2013.01)

(58) Field of Classification Search
CPC .......... A61M 16/0622; A61M 16/0816; A61M 16/0611; A61M 16/0683; A61M 2205/42
See application file for complete search history.

(56) References Cited

U.S. PATENT DOCUMENTS

| | | | |
|---|---|---|---|
| 6,631,718 B1 * | 10/2003 | Lovell | A61M 16/06 128/206.24 |
| 2005/0199242 A1 * | 9/2005 | Matula, Jr. | A61M 16/0816 128/207.13 |

(Continued)

FOREIGN PATENT DOCUMENTS

| | | | | |
|---|---|---|---|---|
| WO | WO2007048174 A1 | 5/2007 | | |
| WO | WO-2009108995 A1 * | 9/2009 | | A61M 16/06 |

(Continued)

*Primary Examiner* — Timothy A Stanis
*Assistant Examiner* — Victoria Murphy
(74) *Attorney, Agent, or Firm* — Michael W. Haas

(57) ABSTRACT

A patient interface includes a cushion having a body with a front portion and a rear portion. The front portion has a lower opening structured to receive a flow of a treatment gas and a coupling mechanism. The rear portion is structured to engage a user's face and provide a generally continuous seal therewith. The patient interface further includes a frame having a torus shaped portion defining an opening. The opening has at least a portion of the coupling mechanism disposed therein.

6 Claims, 17 Drawing Sheets

(56) References Cited

U.S. PATENT DOCUMENTS

| | | | |
|---|---|---|---|
| 2008/0178875 A1* | 7/2008 | Henry | A61M 16/06 128/201.22 |
| 2009/0107508 A1* | 4/2009 | Brambilla | A61M 16/06 128/207.11 |
| 2010/0313891 A1 | 12/2010 | Veliss | |
| 2011/0030692 A1* | 2/2011 | Jones | A61M 16/06 128/206.21 |
| 2012/0234326 A1 | 9/2012 | Mazzone | |
| 2014/0053843 A1* | 2/2014 | Jones, Jr. | A61M 16/0816 128/205.25 |

FOREIGN PATENT DOCUMENTS

| | | | |
|---|---|---|---|
| WO | WO2009108995 A1 | 9/2009 | |
| WO | WO2011060479 A1 | 5/2011 | |
| WO | WO2012028988 A1 | 3/2012 | |

\* cited by examiner

PATIENT INTERFACE DEVICE WITH FRAME AND CLIPS

CROSS-REFERENCE TO RELATED APPLICATIONS

This patent application claims the priority benefit under 35 U.S.C. § 371 of international patent application no. PCT/IB2013/059028, filed Oct. 1, 2013, which claims the priority benefit under 35 U.S.C. § 119 (e) of U.S. Provisional Application No. 61/708,770, filed on Oct. 2, 2012, the contents of which are herein incorporated by reference.

BACKGROUND OF THE INVENTION

1. Field of the Invention

The present invention generally relates to patient interface devices for use in pressure support systems that supply a flow of gas to the airway of a patient and, more particularly, to selected portions of such patient interface devices.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device be simple to use and clean so that a patient would be more likely to utilize the device as prescribed.

Accordingly, a need exists for a patient interface device that improves upon existing devices, for example, to maximize patient comfort while minimizing leak, during delivery of a positive airway pressure or flow of gas to the airway of the user.

SUMMARY OF THE INVENTION

As one aspect of the present invention a patient interface is provided. The patient interface comprises a cushion including a body having a front portion and a rear portion. The front portion has a lower opening structured to receive a flow of a treatment gas and a coupling mechanism. The rear portion is structured to engage a user's face and provide a generally continuous seal therewith. The patient interface further comprises a frame including a torus shaped portion defining an opening, the opening having at least a portion of the coupling mechanism disposed therein.

The frame may comprise a pair of arm members which extend outward from the torus shaped portion. Each arm member may include an upper sub-arm and a lower sub-arm. Each upper sub-arm and each lower sub-arm may define an aperture structured to be coupled to a respective strap of a headgear.

The coupling mechanism may comprise a groove and at least a portion of the torus shaped portion may be disposed in the groove.

The front portion may be structured to be coupled to a coupling device positioned about the lower opening, the coupling device being provided as part of a conduit delivering the flow of treatment gas.

The cushion may be formed as a unitary member with the front portion and the rear portion being portions of the unitary member.

The front portion may be formed from a substantially rigid material.

One or both of the cushion and the frame may include a number of locating features. The number of locating features may include a number of protruding members extending from the front portion of the cushion and a corresponding number of notches formed in the frame.

As another aspect of the present invention, a clip for coupling a headgear strap to a patient interface is provided. The clip comprises: a planar body; an elongated slot defined in the planar body, the elongated slot being structured to receive a portion of the headgear strap therein; and a button member extending from a face of the planar body and terminating in a flared head portion.

The button member may have a generally circular cross-section.

The flared head portion may be of generally planar shape and may be disposed parallel to the planar body.

As a further aspect of the present invention, a coupling mechanism for coupling a headgear strap to a patient interface is provided. The coupling mechanism comprises an aperture defined in a portion of the patient interface and a clip. The clip comprises: a planar body; an elongated slot defined in the planar body, the elongated slot being structured to receive a portion of the headgear strap therein; and a button member extending from a face of the planar body and terminating in a flared head portion, the button member being disposed in the aperture.

The aperture may comprise a first portion generally elongate in shape and a second portion generally circular in shape.

The portion of the patient interface may comprise a frame.

The frame may comprise a pair of arm members extending outward from a torus shaped portion, each arm member including an upper sub-arm and a lower sub-arm, with the aperture being defined in at least one of the lower sub-arms.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are provided for the purpose of illustration and description only and are not intended as a definition of the limits of the invention.

DETAILED DESCRIPTION OF THE EXEMPLARY EMBODIMENTS

Figure 1:
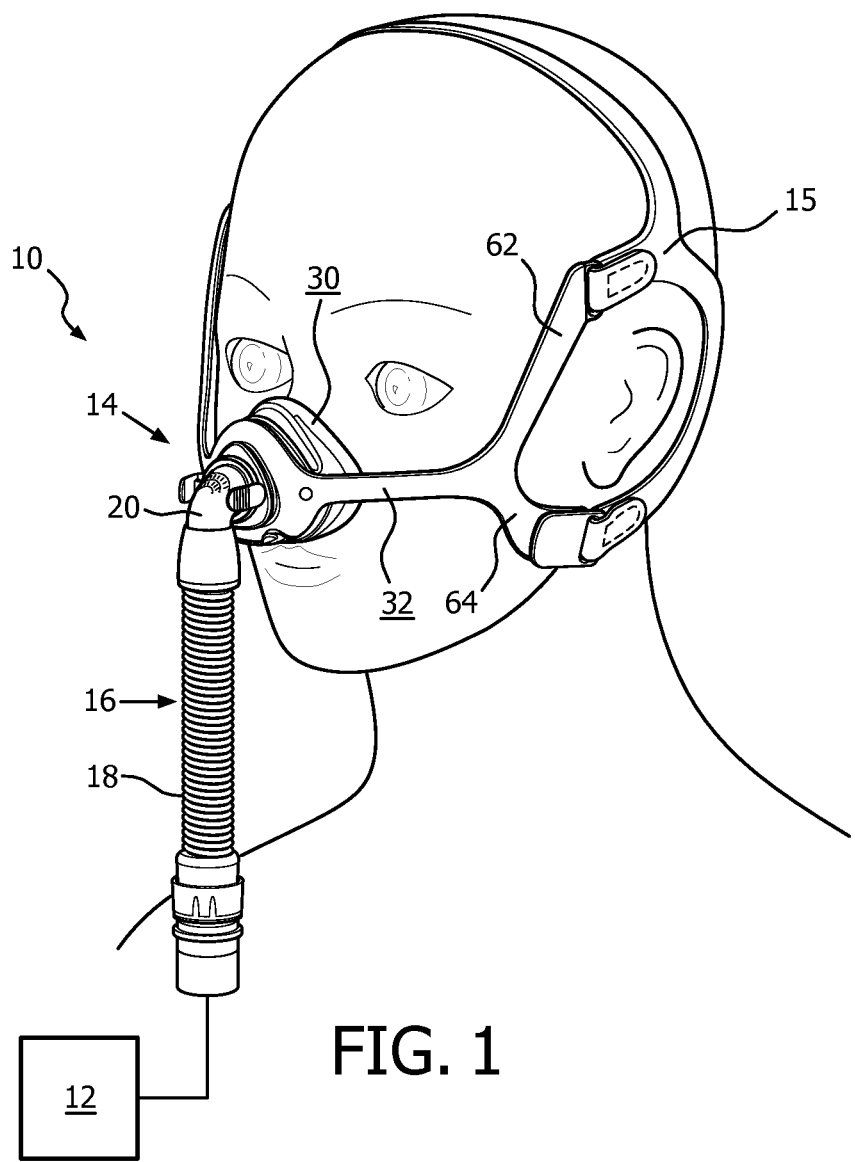
FIG. 1 is a partially schematic view of a system adapted to provide a regimen of respiratory therapy to a patient and includes an isometric view of an example patient interface device in accordance with the principles of the present invention with a portion shown disposed on the head of a patient.
Figure 1B:
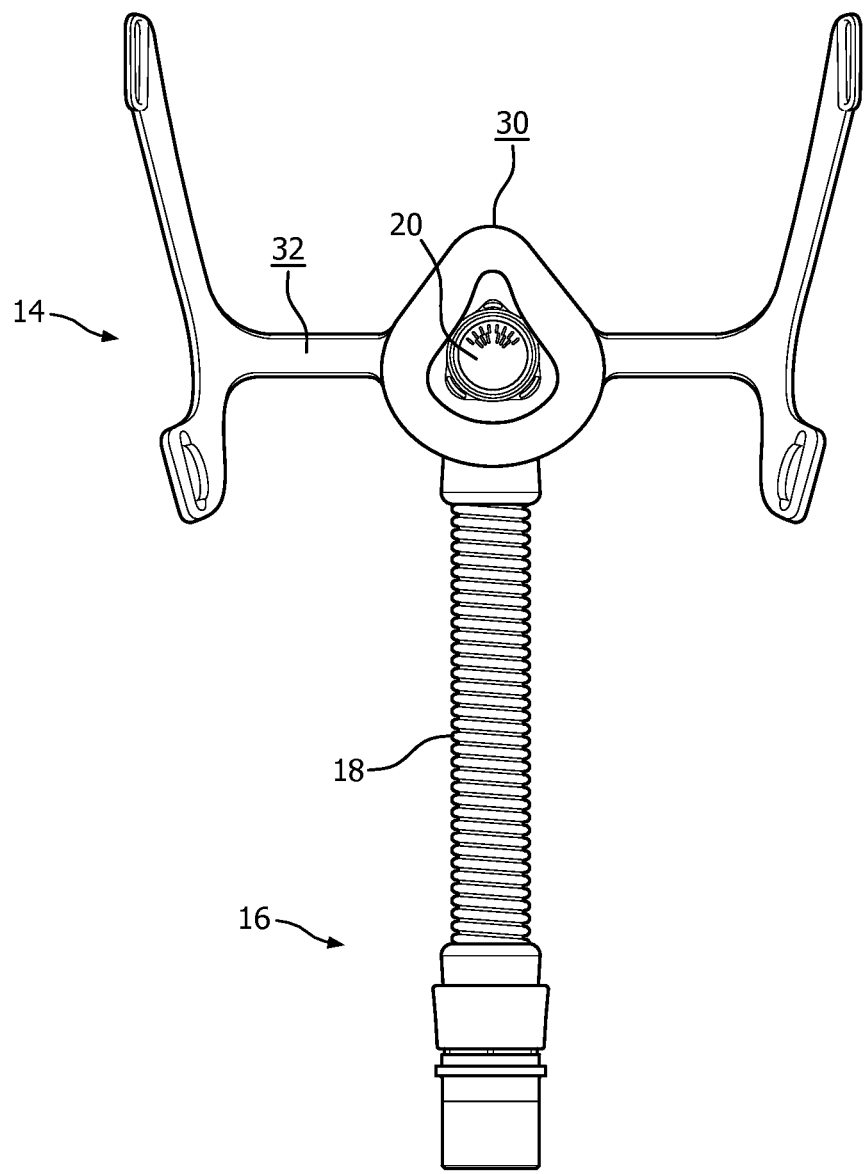
FIG. 1B is a rear (patient side) view of the patient interface and a portion of the patient circuit of FIG. 1.
Figure 1C:
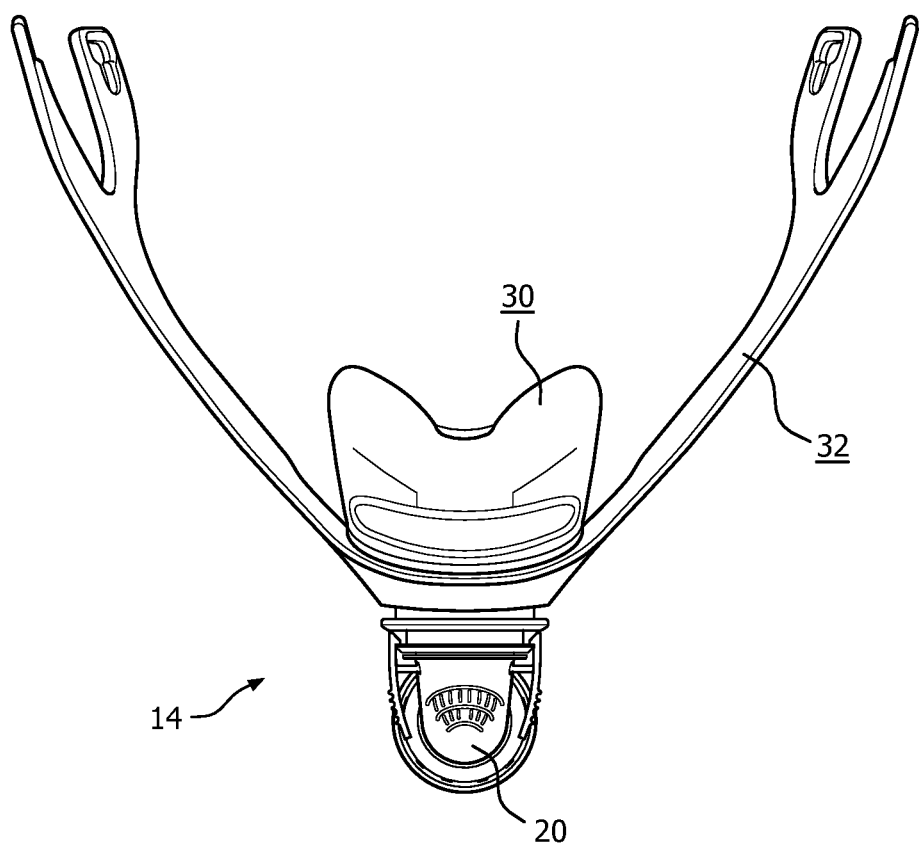
FIG. 1C is a top view of the patient interface and a portion of the patient circuit of FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality) and the singular form of "a", "an", and "the" include plural referents unless the context clearly indicates otherwise.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 10 adapted to provide a regimen of respiratory therapy to a patient is generally shown in FIG. 1. System 10 includes a pressure generating device 12 (shown schematically); a patient interface device 14 shown disposed on, and secured to, the head of a patient (not numbered) via a headgear 15; and a patient circuit 16 (partially shown schematically). Although system 10 is discussed as including pressure generating device 12, patient interface 14 and patient circuit 16, it is contemplated that other systems may be employed while remaining within the scope of the present invention. Also, it is to be understood that although shown with an example headgear 15, such headgear is provided for example purposes only and that other headgear may be employed without varying from the scope of the present concept.

Pressure generating device 12 is structured to generate a flow of breathing gas and may include, without limitation, ventilators, constant pressure support devices (such as a continuous positive airway pressure device, or CPAP device), variable pressure devices (e.g., BiPAp®, Bi-Flex®, or C-Flex™ devices manufactured and distributed by Philips Respironics of Murrysville, Pa.), and auto-titration pressure support devices.

Patient circuit 16 is structured to communicate the flow of breathing gas from pressure generating device 12 to patient interface device 14. Typically, patient circuit 16 includes a conduit or tube which couples pressure generating device 12 and patient interface device 14. In the example embodiment illustrated in FIGS. 1 and 2, patient circuit 16 includes a conduit 18 (shown partially schematically) and an elbow 20 coupled to patient interface device 14.

Figure 2:
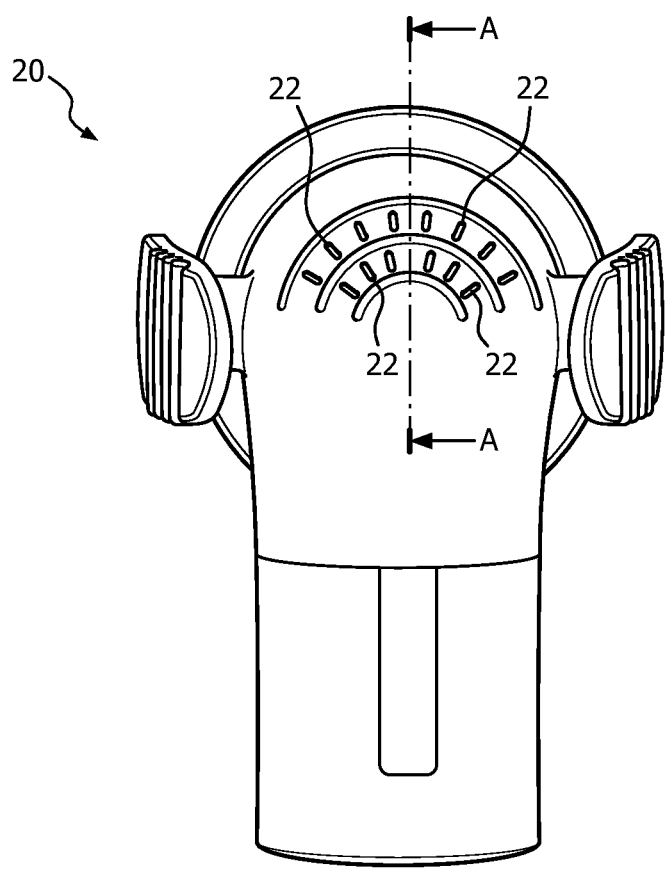
FIG. 2 is a front elevation view of the elbow of the system of FIG. 1.
Figure 3:
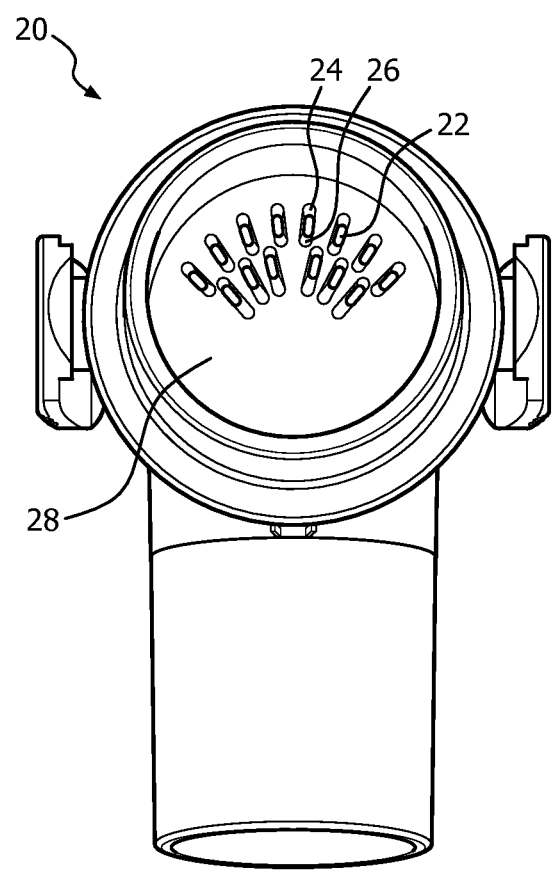
FIG. 3 is a rear elevation view of the elbow of FIG. 2.
Figure 4:
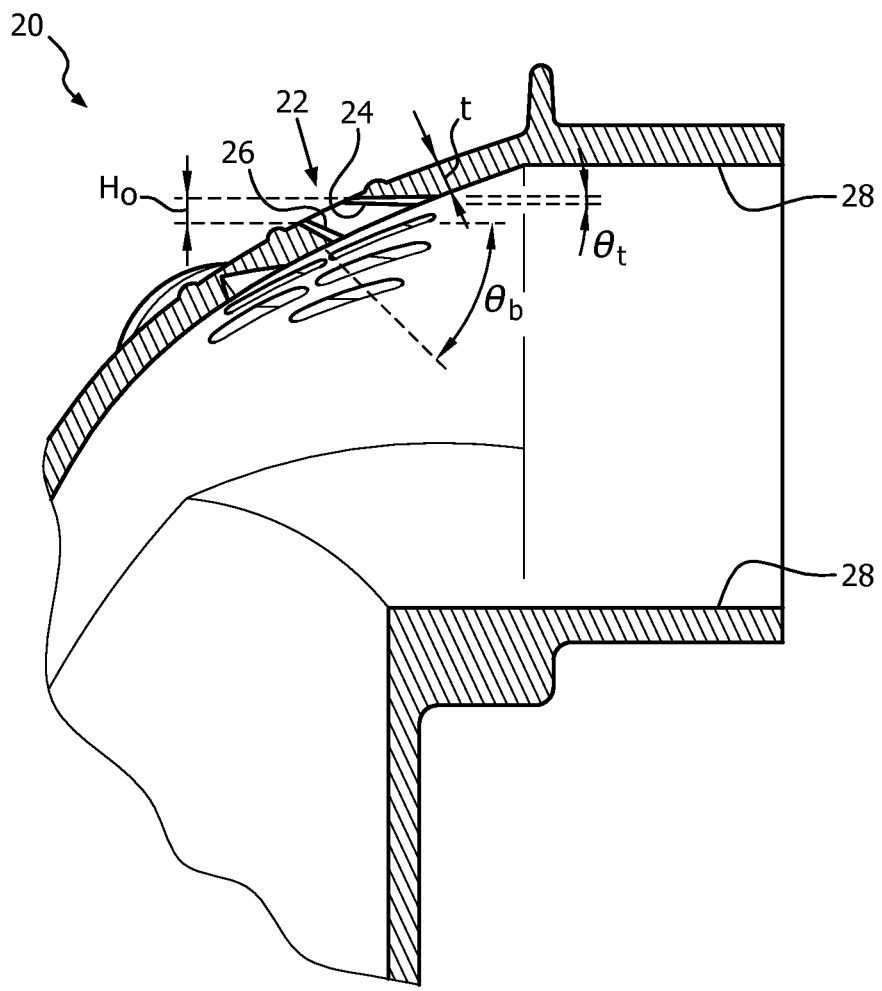
FIG. 4 is a cross-sectional view of the elbow of FIGS. 2 and 3 taken along line A-A of FIG. 2.
Figure 5:
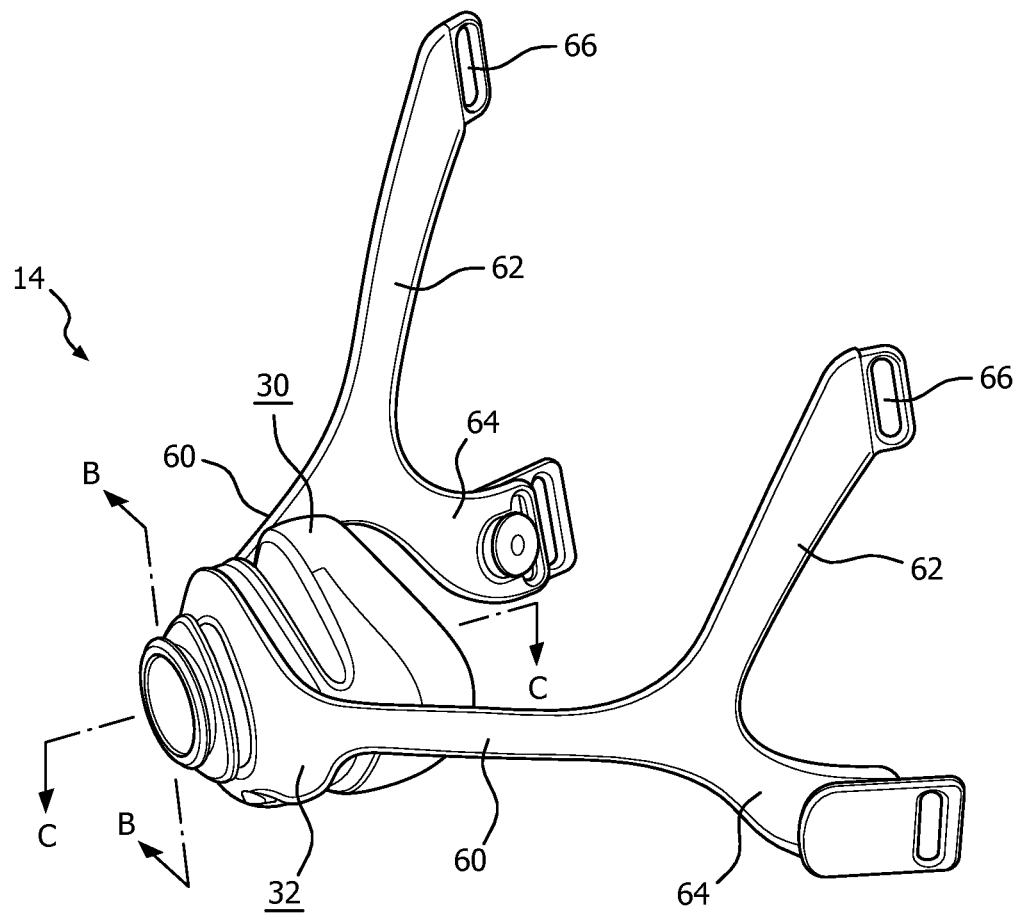
FIG. 5 is an isometric view of the patient interface of the system of FIG. 1.

Referring to FIGS. 2-4, elbow 20 includes a plurality of exhalation ports 22 formed therein which are adapted to vent gases exhaled by the patient in a desired manner. The positioning of exhalation ports 22 on the compound curved surface of elbow 20 accomplishes diffusion of exhaust gases. As shown in the cross-sectional view of FIG. 4, each exhalation port 22 has a tapered cross-section having an outer height $H_o$ which acts as the primary control for the flow rate of exhaust air out of system 10 and is sized to ensure that minimum safety values are met (e.g., adequate $CO_2$ flushing) across a range of pressures. Other dimensional factors that act as secondary controls to the flow rate exiting through each exhalation port 22 are the angle $\theta_t$ of the top portion 24, the angle $\theta_b$ of the bottom portion 26, and the wall thickness t of the portion of elbow 20 where exhalation portions 22 are disposed. For example, larger angles and a thinner wall allows for more leak from smaller apertures, with lower noise.

In the example embodiment illustrated in FIGS. 2-4, upper portion 24 is oriented at an angle $\theta_t$ that as large as possible without creating issues for the manufacturing process. Bottom portion 26 is oriented at a significantly steeper angle $\theta_b$ (approx. 30°) in order to provide for better diffusion of exhaust gases. It is to be appreciated that such arrangement and geometry of exhalation ports 22 provides for a design which is easier to manufacture than conventional exhaust port designs and that also provides for a high diffusion and low noise mechanism for venting exhalation gases from system 10.

In order to reduce noise resulting the flow of breathing gas provided by pressure generating device 12, the inner surfaces 28 (FIGS. 3 and 4) of elbow 20 are provided with a textured finish which provides for a slightly turbulent flow. In an example embodiment, inner surfaces 28 of elbow 20 were provided with a MT-11010 textured surface finish provided by Mold-Tech®, although other textured surface finishes may be employed without varying from the scope of the present invention.

Referring to FIGS. 5-10, patient interface device 14 includes a cushion 30 and a frame 32. Cushion 30 includes a body 33 with a front portion 34 and a rear portion 36, discussed below. In an exemplary embodiment, front portion 34 is substantially rigid (e.g., without limitation, formed from a polycarbonate material). In an exemplary embodiment, front portion 34 is a single piece structured to cover the user's nose. That is, cushion 30 has a peripheral contour that is structured to extend over a user's nose. In this embodiment, body 33 is coextensive with front portion 34. It is understood that this is an exemplary embodiment and cushion 30 may be structured to extend over the user's nose and mouth, or, just the user's mouth. Further, it is understood that the front portion 34 may be made from a soft or flexible material separately from, or integrally with rear portion 36 (i.e., in such example cushion 30 is formed as a unitary member), and thus also may be formed from the same or a different material or materials than rear portion 36.

Front portion 34 defines a lower opening 38 which functions as a gas inlet and outlet for cushion 30. As shown in FIG. 1, elbow 20 can be selectively coupled to front portion 34 about lower opening 38 for supplying the flow of treatment gas produced by pressure generating device 12 to the inner portion (not numbered) of cushion 30. Although illustrated with elbow 20, it is to be appreciated that the present invention contemplates a variety of different coupling devices that could be coupled, either permanently or selectively, to front portion 34 about or to lower opening 38 to carry gas to or from cushion 30. Thus, a variety of coupling devices (e.g., with or without swivels on one or both ends, and with or without an exhalation system formed integral to the device) may be substituted for elbow 20.

Front portion 34 of cushion 30 further includes a coupling mechanism 40 structured to provide for the selective coupling of cushion 30 and frame 32, such as shown, for example, in FIGS. 1, 5, 7 and 8. For frame 32, coupling mechanism 40 is a coupling structured to interface with a closed, flexible loop or torus shaped portion 44 which defines an opening 46 through which a portion of coupling mechanism 40 of cushion 30 is disposed therein, as discussed below. Accordingly, mask coupling mechanism 40 may be a loop-like channel or groove 47 in front portion 34. Groove 47 extends inward into front portion 34 in a direction that is generally perpendicular to the direction of compression forces exerted by frame 32 on cushion 30 when patient interface 14 is disposed on a user, such as shown in FIG. 1.

The outer edge of groove 47 has a greater cross-sectional area than torus shaped portion 44 and frame 32 must be deformed to pass over front portion 34 of cushion 30 so that torus shaped portion 44 may be disposed in the groove. Further, the contour of the outer surface of front portion 34 of cushion 30 may form a platform 48. Platform 48 is structured to abut, and thereby effect, the shape of frame 32. Further, front portion 34 of cushion 30 may include a retaining flange 50 extending partially over platform 48. In an exemplary embodiment, retaining flange 50 extends generally parallel to platform 48, thus forming groove 47. Accordingly, if platform 48 is concave relative to the user's face, then retaining flange 50 may also be concave relative to the user's face. However, retaining flange 50 may also be generally planar in shape regardless of the shape of platform 48.

Rear portion 36 of cushion 30 is structured to extend from front portion 34 toward the user's face and generally defines the depth of cushion 30. Rear portion 36 is made from a flexible material and is structured to engage the user's face and provide a generally continuous seal therewith. This seal may be improved to be a more complete seal if cushion 30 is maintained in an orientation that is generally tangent relative to the user's face. The bias that causes cushion 30 to engage the user's face is created by frame 32.

In order to minimize rotational movement between cushion 30 and frame 32 opening 46 in frame 32 and groove 47 in cushion 30 may be of non-circular shape. As another or as an additional mechanism for minimizing such rotational movement, one or more locating features may be provided on one or both of the cushion 30 and frame 32. In the example embodiment illustrated in FIGS. 5-10, and more particularly in FIGS. 9 and 10, a pair of protruding members 52 are provided on a lower portion of platform 48 which cooperative engage a corresponding pair of notches 54 formed in frame 32. Although shown as having two protruding members 52 and corresponding notches 54, it is to be appreciated that such features are provided for illustrative purposes only and that one or more of the size, shape, quantity, and/or placement (with respect to location on one or both of cushion 30 and frame 32) of such features may be varied without varying from the scope of the present concept.

Figure 6:
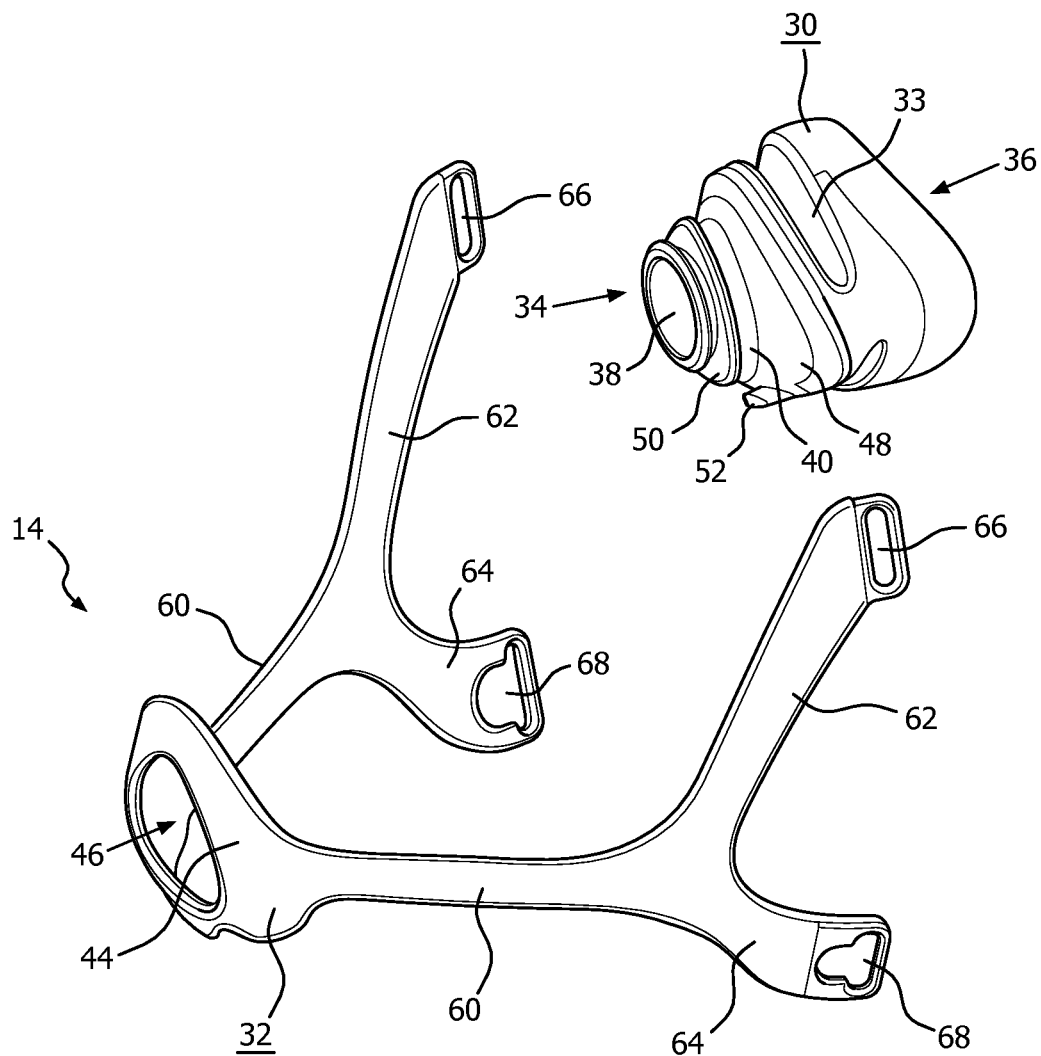
FIG. 6 is an exploded isometric view of the patient interface of the system of FIG. 1.
Figure 7:
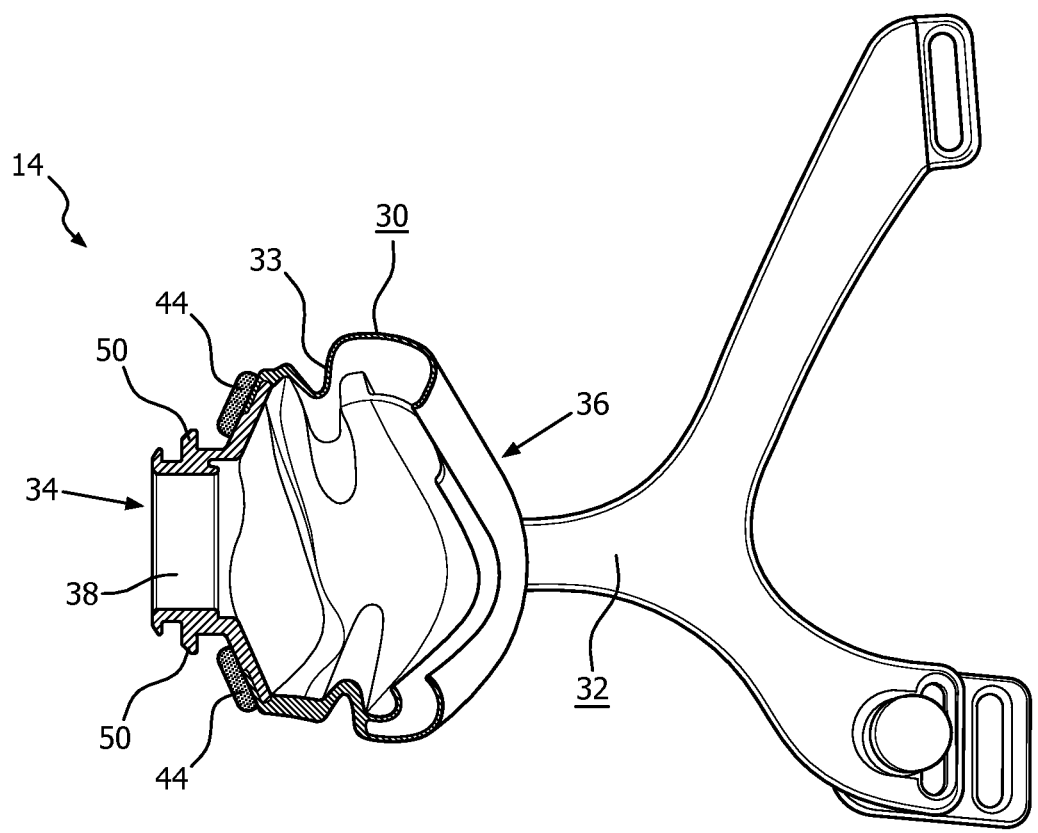
FIG. 7 is a cross-sectional view of the patient interface of FIG. 5 taken along line B-B of FIG. 5.
Figure 8:
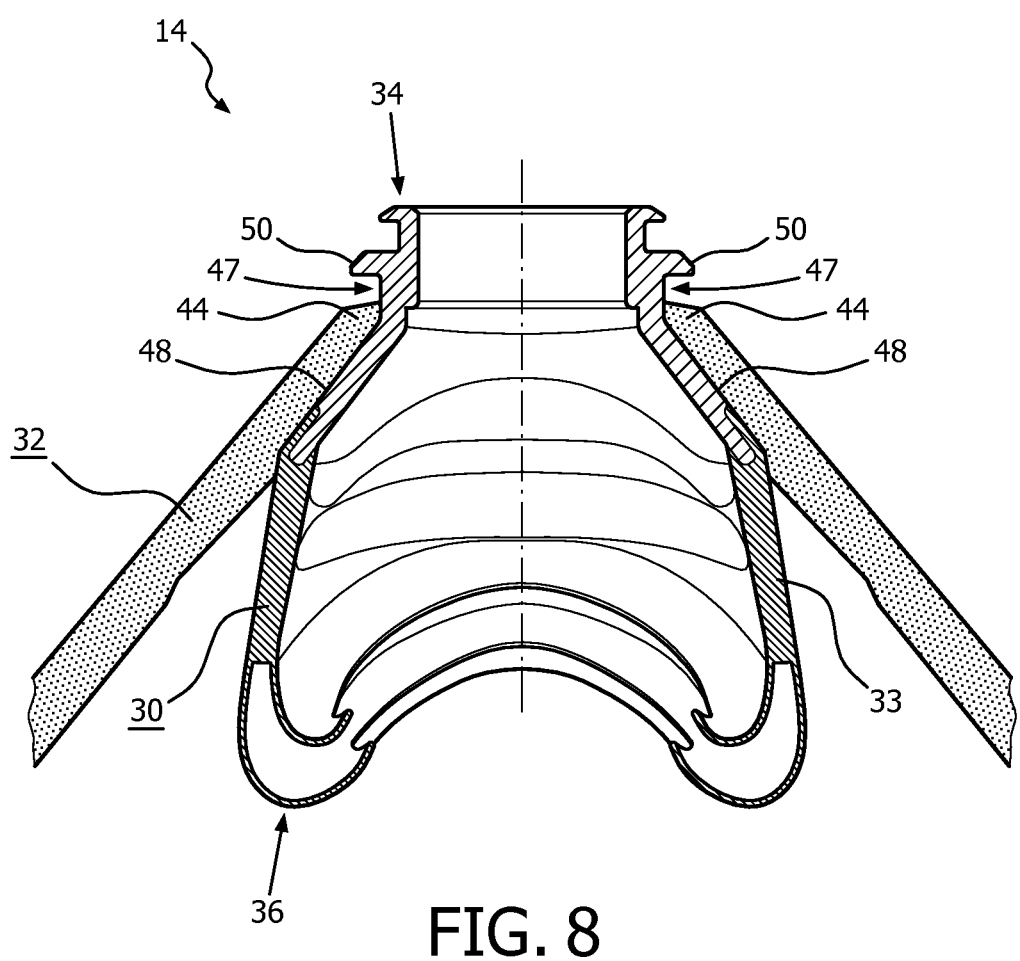
FIG. 8 is another cross-sectional view of the patient interface of FIG. 5 taken along line C-C of FIG. 5.
Figure 9:
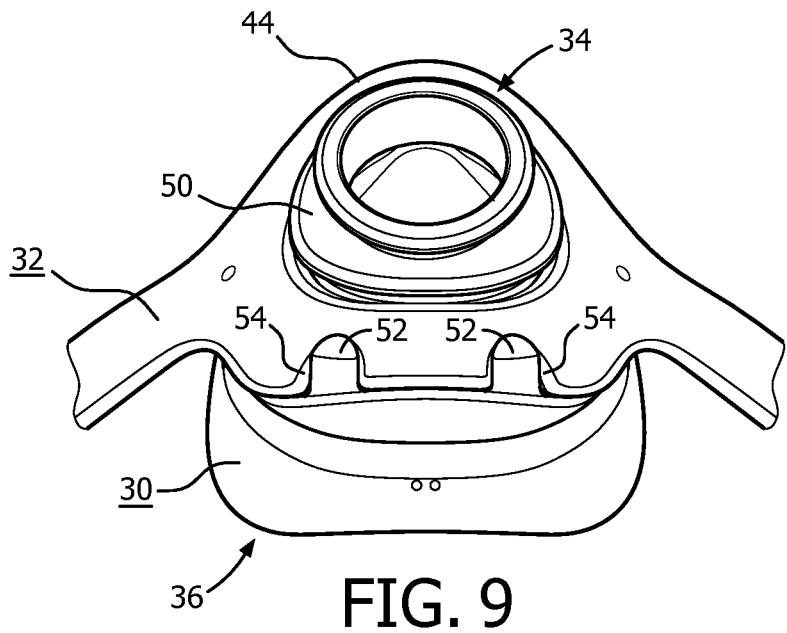
FIG. 9 is an isometric view of the lower side of the patient interface of the system of FIG. 1.
Figure 10:
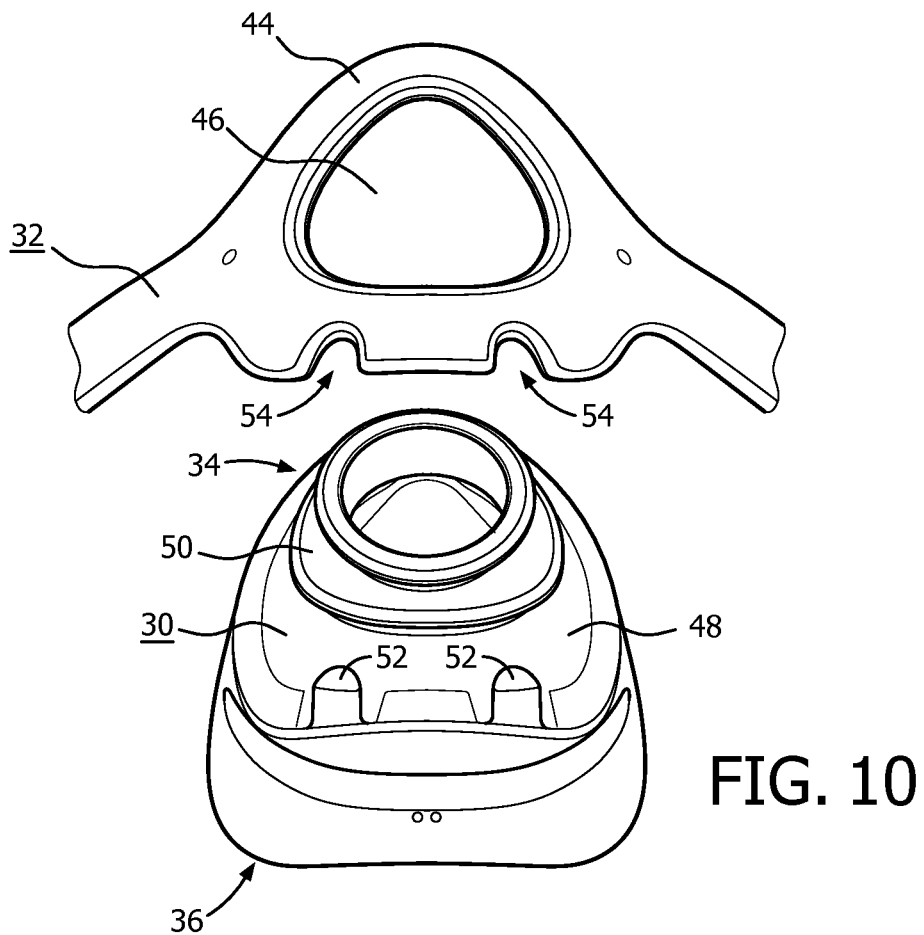
FIG. 10 is an exploded isometric view of the lower side of the patient interface of the system of FIG. 1.

Referring to FIG. 6, frame 32 includes a pair of arm members 60 which extend outward from torus shaped portion 44. In the example embodiment illustrated in the FIGS., each arm member 60 splits into two sub-arms, upper sub-arm 62 and lower sub-arm 64 that define upper aperture 66 and lower aperture 68, respectively, at or about ends thereof, to which straps of a headgear, e.g., without limitation, headgear 15 of FIG. 1, may be coupled.

Upper aperture 66 is generally elongate in shape and is structured to accept a strap from a head gear which, as shown in the example of FIG. 1, may then be adjustably coupled back upon itself, such as through the use of Velcro® or other suitable fastening mechanism.

Figure 11:
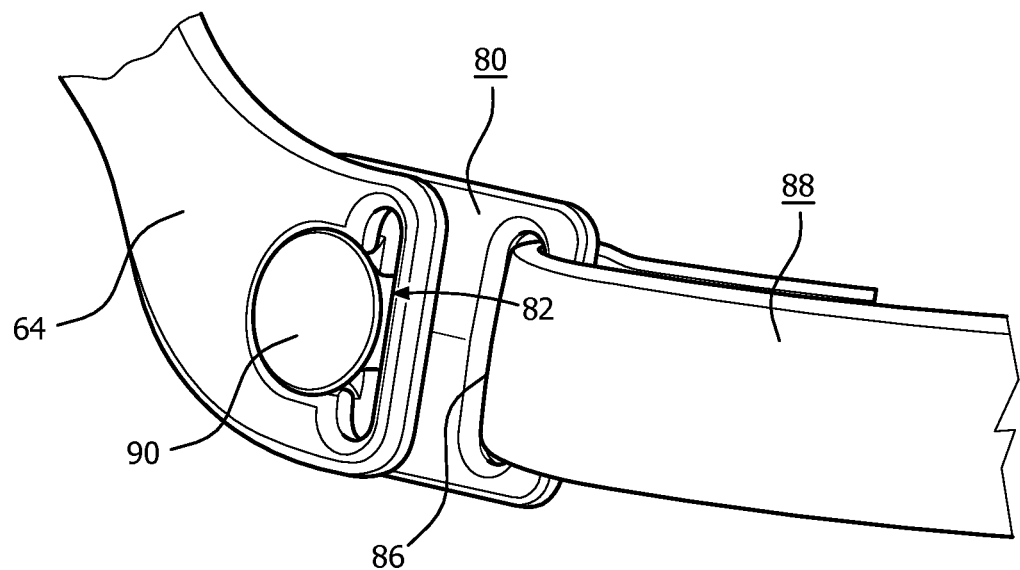
FIG. 11 is a detail isometric view of an example frame and headgear connection (both partially shown) in accordance with the principles of the present invention.
Figure 11B:
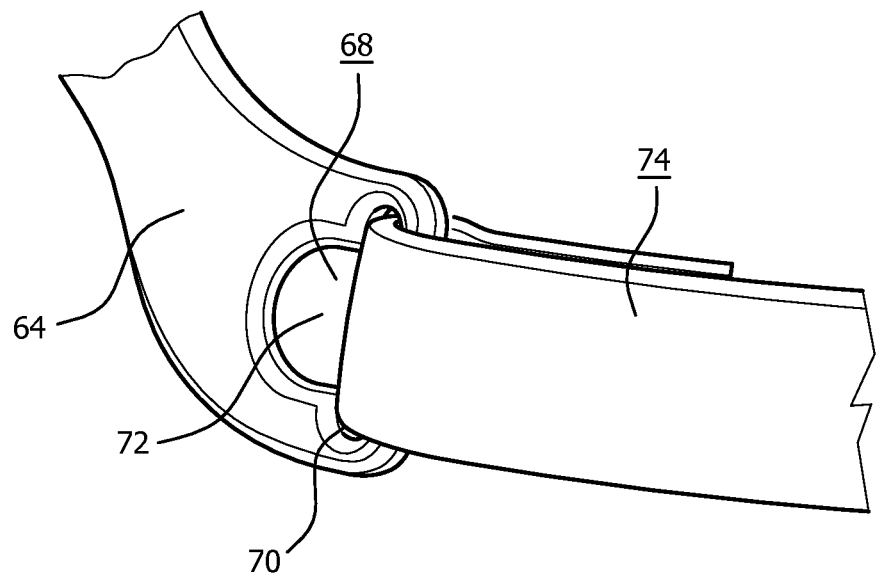
FIG. 11b is a detail isometric view of an alternate example frame and headgear connection (both partially shown) in accordance with the principles of the present invention.
Figure 12:
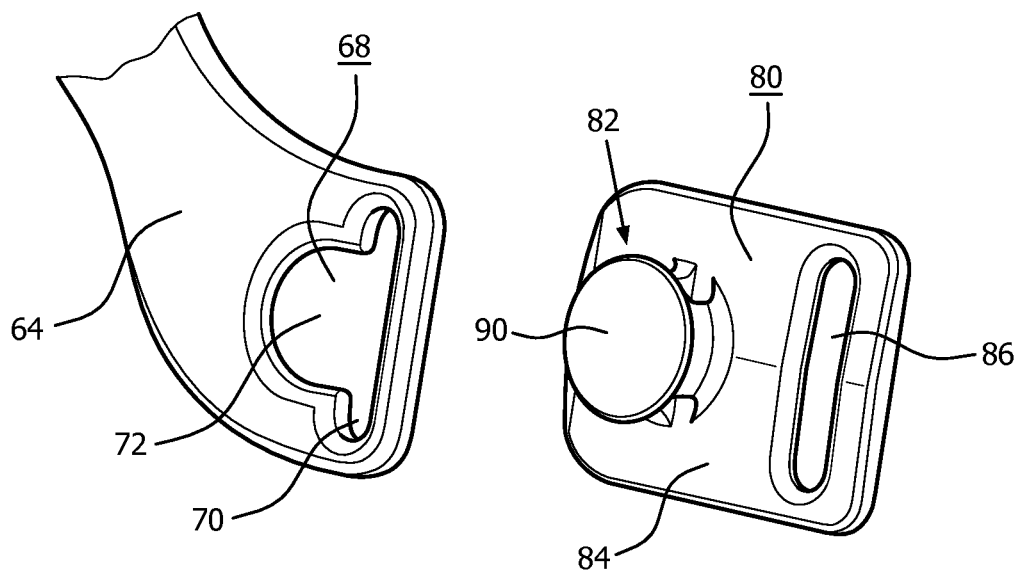
FIG. 12 is an exploded view of the isometric view of FIG. 11.

As shown in the detailed view of FIG. 12, lower aperture 68 includes a first portion 70, which is generally elongate in shape, and a second portion 72, which is generally circular in shape. As shown in FIG. 11, second portion 72 of aperture 68 is adapted to receive a button member 82 of a headgear clip 80, discussed in further detail below. Alternately, first portion 70 of aperture 68 is structured to receive a strap in a similar manner as upper aperture 66 previously described. FIG. 11b shows an example of a strap 74 received in, and engaged, with first portion 70 of aperture 68. It is to be appreciated that aperture 68 thus provides for either direct coupling of frame 32 (or other member in which aperture 68 is formed) to a headgear strap or alternately to indirect coupling of frame 32 (or other member in which aperture 68 is formed) via headgear clip 80 (described in detail below) to a headgear strap.

Figure 13:
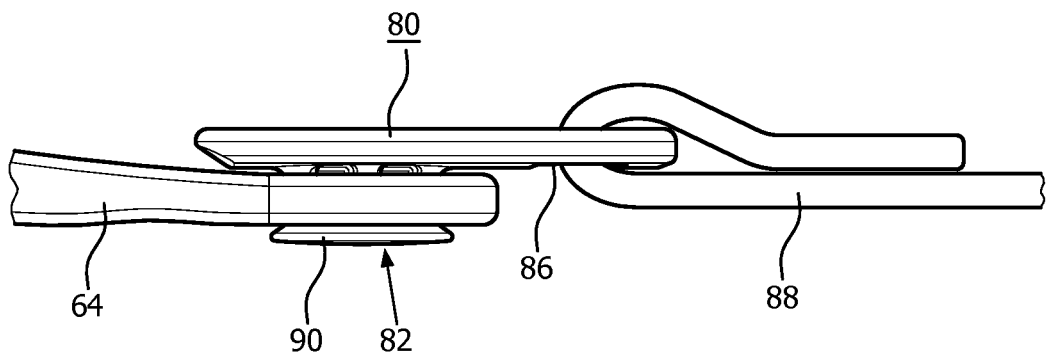
FIG. 13 is a top edge view of the connection shown in FIG. 11.
Figure 14:
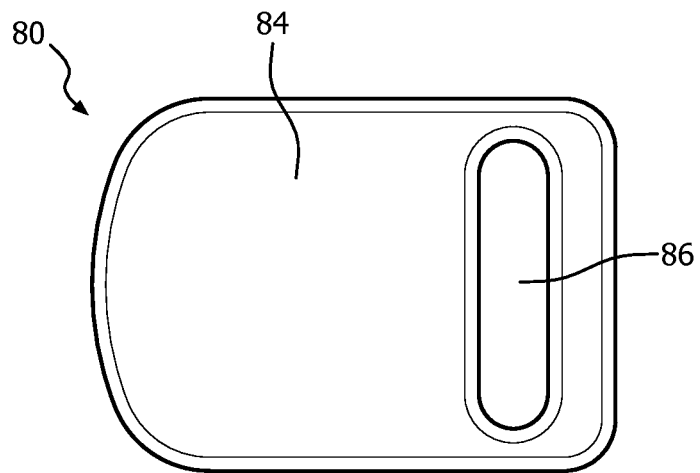
FIGS. 14-16, respectively, illustrate top, side and bottom views of an example clip member in accordance with the principles of the present invention for use in selectively coupling a headgear and frame.
Figure 15:
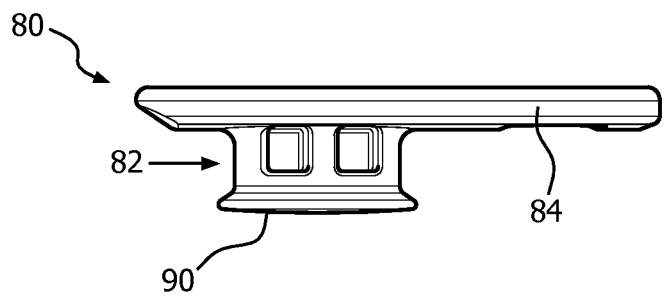
Figure 16:
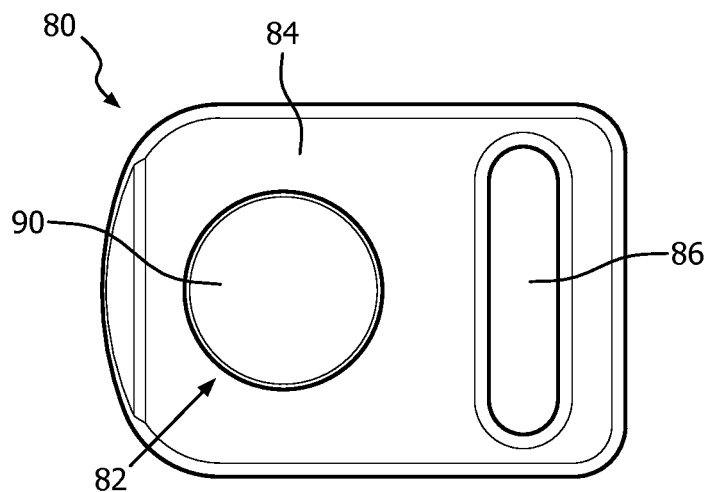

Headgear clip 80 is formed from a rigid or semi-rigid material (e.g., without limitation, thermoplastic, thermoplastic elastomer, thermoset, metal). Referring to FIGS. 14-16, headgear clip 80 includes a generally thin, planar body 84 having an elongated slot or aperture 86 formed therein. Aperture 86 is structured to receive a strap in a similar manner as upper aperture 66 and first portion 70 of aperture 68 as previously described. FIGS. 11 and 13 show examples of a strap 88 received in, and engaged with, aperture 86. Headgear clip 80 further includes button member 82 which has a generally circular cross-section and extends from a face (not numbered) of planar body 84 and terminates in a flared head portion 90. As perhaps best shown in FIGS. 13 and 15, head portion 90 of button member 82 is generally planar in shape and is disposed generally parallel to planar body 84. Head portion 90 is sized slightly larger than the corresponding portion of aperture 68. Such arrangement provides for button member 82 to generally "snap" in or out of second portion 72 of aperture 68 through slight deformation of one or both of aperture 68 and head portion 90. It is to be appreciated that headgear clip 80 provides for a low-profile, quick-coupling/release mechanism for easily removing and installing a headgear and patient interface on the head of a user without requiring readjustment while still providing for initial adjustability of a strap with respect to headgear clip 80. It is also to be appreciated that the generally circular cross-section of button member 82 allows for rotational movement of headgear clip 80 (and the associated strap) with respect to frame 32, which thus provides for improved fitment of the related headgear.

Although the example embodiment described herein has a generally circular cross-section, it is to be appreciated that button member 82 may be formed having other, non-circular cross sections without varying from the scope of the present invention. In such embodiments, the non-circular button member is employed with a corresponding shaped aperture. Although such non-circular arrangement does not allow for rotation of the headgear clip with respect to the corresponding non-circular aperture, such arrangement does still provide for a low profile coupling mechanism that provides for quick release/attachment.

Figure 17:
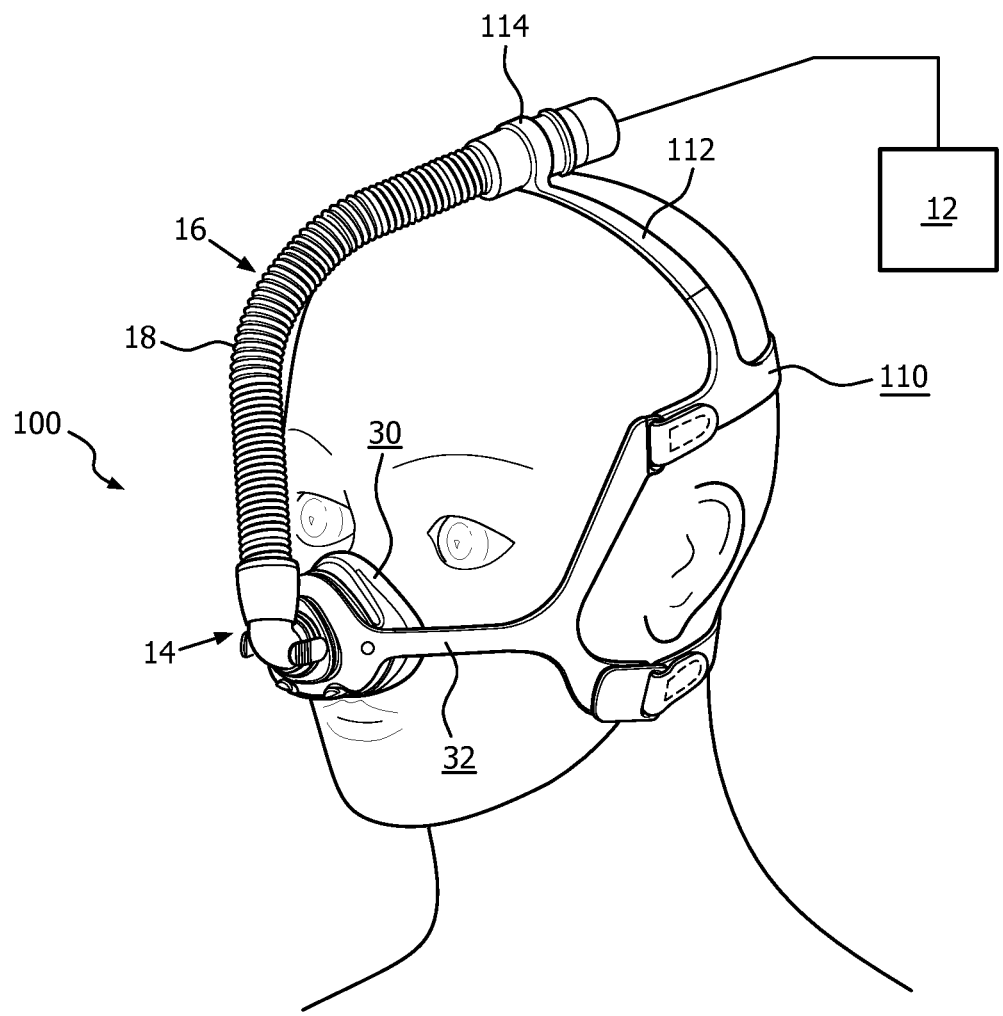
FIG. 17 shows a partially schematic view of another system adapted to provide a regimen of respiratory therapy to a patient and includes an isometric view of the patient interface device of FIG. 1 disposed on the head of a patient and secured via an example headgear assembly in accordance with the principles of the present invention.

FIG. 17 illustrates another example system 100 (shown partially schematically) that is adapted to provide a regimen of respiratory therapy to a patient. System 100 includes generally the same components as system 10, previously described in connection with FIG. 1, except patient interface 14 is coupled to the head of a patient via a headgear assembly 110. Headgear assembly 110 includes an upper strap 112 which includes a loop 114 structured to receive conduit 18 therethrough such that conduit 18 may be generally secured to the top of the patient's head. In an example embodiment, loop 114 is formed from an elastic material (e.g., without limitation, spandex, nylon) so as to fit snugly about conduit 18. Also, in an example embodiment loop 114 is further structured to collapse generally flat when conduit 18 is not disposed therein. It is to be appreciated that such arrangement generally provides for conduit 18 to be secured to the patient in a reliable manner that allows for general movements of a patient (e.g., without limitation, rolling over during sleep) while inhibiting unwanted tension on conduit 18 and thus unwanted gas leakage from cushion 30 and/or general discomfort to the patient.

Figure 18:
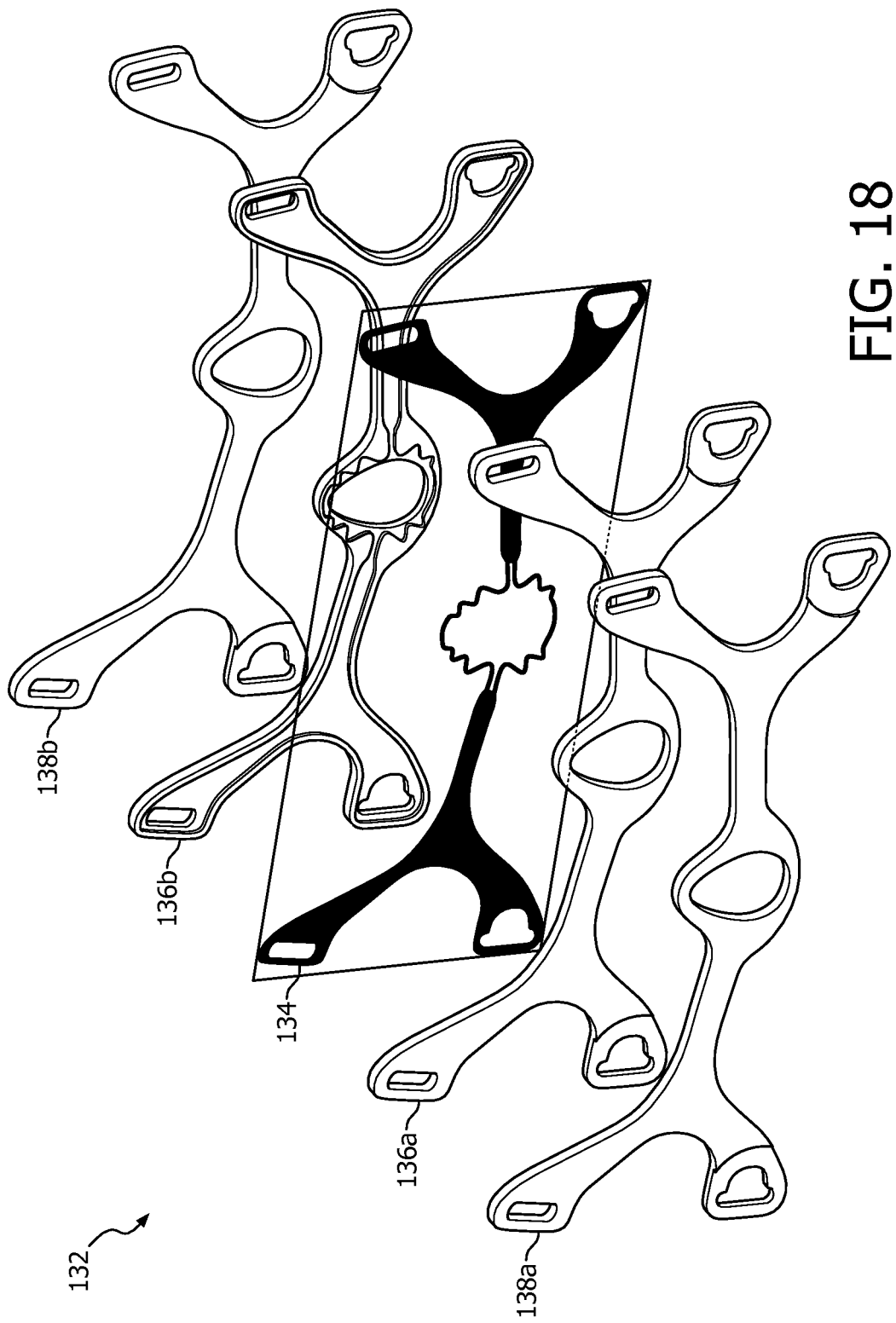
FIG. 18 is an exploded view of a further embodiment for a frame according to the principles of the present invention.
Figure 19:
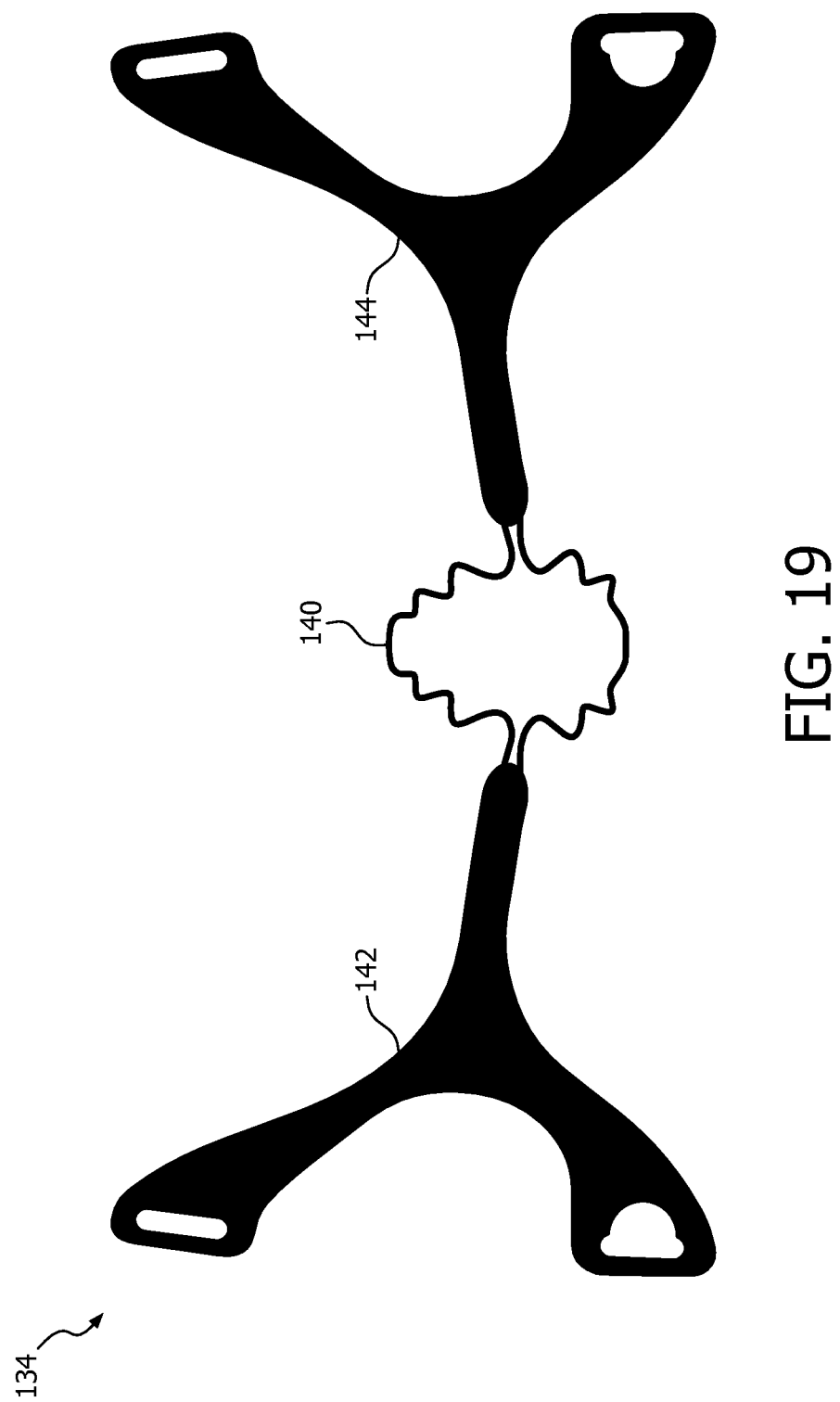
FIG. 19 is a side view of a support member for use in a frame according to the principles of the present invention.

FIGS. 18 and 19 illustrate a further embodiment for a frame 132 according to the principles of the present invention. Frame 132 can be used in place of frame 32 in the previous embodiment. In this exemplary embodiment, frame 132 includes a layered structure that includes as its central portion a support member 134. On each side of support member 134 is a foam member 136a and 136b, each of which is covered by an optional layer fabric 138a and 138b. As a result, at least a central portion 140 of support member 134 is completely enclosed.

As shown in FIG. 19, support member 134 is formed from a semi-rigid material, such as plastic and includes end portions 142 and 144 on either side of central portion 140. In the exemplary embodiment, central portion 140 is formed as a relatively thin flexible wire or cable so that central portion 140 is more flexible than the remainder of the frame. Central portion 140 can have any shape or configuration in addition to that shown so long as the desired flexibility for the central hub of the frame is achieved. The present invention contemplates that support member 134 can be injection molded, stamped, or cut out. It can be formed from a unitary material or from a composition of materials. For example, end portions 142 and 144 can be formed from a material that is different than that used to form central portion 140.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A patient interface comprising:
   (a) a cushion including a body having a front portion and a rear portion, the front portion including a tubular extension having a lower opening structured to receive a flow of a treatment gas and a coupling mechanism, the rear portion being structured to engage a face of a user and provide a generally continuous seal therewith; and (b) a frame including a central portion defining a frame opening and a pair of arm members extending outward from the central portion, wherein each arm member is sized and configured to extend past a respective eye of a patient on which the patient interface is positioned and then split into an upper sub-arm that is sized and configured to extend toward a first portion of the patient's head above an ear of the patient and a lower sub-arm that is sized and configured to extend toward a second portion of the patient's head below the ear of the patient, wherein a slot is defined in each upper sub-arm, and wherein a first coupling mechanism is disposed on each lower sub-arm, and (c) a headgear, including:
  (1) first headgear strap portions inserted into each slot on each upper sub-arm and second headgear strap portions;
  (2) the second headgear strap portions adapted to be selectively coupled to each lower sub-arm;
  (3) a pair of headgear clips, each headgear clip including: a clip slot defined therein, and a second coupling mechanism, wherein each second headgear strap portion is inserted into a respective clip slot, and wherein the first coupling mechanism and the second coupling mechanism cooperate to engage each headgear clip to each lower sub-arm.

2. The patient interface of claim 1, wherein the front portion is structured to be coupled to a coupling device positioned about the lower opening, the coupling device being provided as part of a conduit delivering the flow of the treatment gas.

3. The patient interface of claim 1, wherein the cushion is formed as a unitary member and the front portion and the rear portion are portions of the unitary member.

4. The patient interface of claim 1, wherein the front portion is formed from a material having a greater rigidity than the rear portion.

5. The patient interface of claim 1, wherein one or both of the cushion and the frame include a number of locating features.

6. The patient interface of claim 5, wherein the number of locating features include a number of protruding members extending from the front portion of the cushion and a corresponding number of notches formed in the frame.

* * * * *